United States Patent [19]

Fischer et al.

[11] Patent Number: 4,910,304

[45] Date of Patent: Mar. 20, 1990

[54] PREPARATION OF N-SUBSTITUTED CYCLIC AMINES

[75] Inventors: Roman Fischer, Mutterstadt; Herbert Mueller, Frankenthal; Dieter Voges, Mannheim, all of Fed. Rep. of Germany

[73] Assignee: BASF Aktiengesellschaft, Ludwigshafen, Fed. Rep. of Germany

[21] Appl. No.: 331,942

[22] Filed: Mar. 31, 1989

[30] Foreign Application Priority Data

Apr. 20, 1988 [DE] Fed. Rep. of Germany ....... 3813169

[51] Int. Cl.⁴ ................. C07D 265/30; C07D 295/02; C07D 295/08
[52] U.S. Cl. .................................... 544/178; 540/450; 540/467; 540/544; 540/609; 540/611; 540/612; 544/177; 546/184; 546/192; 546/236; 546/248; 548/574; 548/577; 548/578; 548/579
[58] Field of Search ............... 540/450, 467, 544, 609, 540/612, 611; 544/177, 178; 546/184, 192, 236, 248; 548/574, 578, 579, 577

[56] References Cited

U.S. PATENT DOCUMENTS

| | | | |
|---|---|---|---|
| 3,151,113 | 2/1962 | Advani et al. | 544/178 |
| 3,167,551 | 1/1965 | Welpert | 544/178 |
| 3,709,881 | 1/1973 | Warner | 544/178 |

FOREIGN PATENT DOCUMENTS 1106084 3/1968 United Kingdom .

Primary Examiner—Robert W. Ramsuer
Attorney, Agent, or Firm—John H. Shurtleff

[57] ABSTRACT

N-substituted cyclic amines of the general formula I

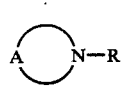

I where A is an alkylene group or a $-(CH_2)_n-[-O-(CH_2)_m]_r$ group which may be monosubstituted or polysubstituted by radicals R without the radicals R in a defined compound having to be identical, R is alkyl, alkoxyalkyl, unsubstituted or alkyl-substituted or alkoxy-substituted cycloalkyl, cycloalkylalkyl, aryl or arylalkyl, n and m independently of one another are each from 2 to 8 and r is from 1 to 3, the $-(CH_2)_n-[O-(CH_2)_m]_r$ group consisting of from 5 to 12 members, are prepared by reacting a primary amine of the general formula II

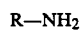

R—NH₂ (II)

with a diol of the general formula III

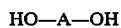

HO—A—OH (III)

where R and A have the abovementioned meanings, and hydrogen in the presence of a copper-containing hydrogenation/dehydrogenation catalyst at elevated temperatures and under superatmospheric pressure, by a process in which the reaction is carried out in the presence of a catalytic amount of a basic alkali metal compound or alkaline earth metal compound.

7 Claims, No Drawings

PREPARATION OF N-SUBSTITUTED CYCLIC AMINES

The present invention relates to a novel and improved process for the preparation of N-substituted cyclic amines by reacting a primary amine with a diol in the presence of a hydrogenation/dehydrogenation catalyst.

U.S. Pat. No. 3,167,551 and BE-A-No. 691 068 disclose that N-alkylated heterocyclic amines can be obtained by reacting diols with ammonia and then methylating the product with formaldehyde or methanol under hydrogenating conditions.

U.S. Pat. No. 3,151,113 discloses that N-alkylated morpholines can be prepared by reacting the corresponding diol with ammonia and methanol in the presence of hydrogen over a hydrogenation/dehydrggenation catalyst.

According to U.S. Pat. No. 3,709,881 and GB-A-No. 1 106 084, N-alkylmorpholines are likewise obtainable from the corresponding diol and the corresponding amines. Recommended catalysts include copper, nickel, cobalt or chromium, mixtures of these and oxides or carbonates of these metals.

All these processes are unsatisfactory in terms of their range of applications or the yields obtained.

Furthermore, EP-A-No. 137 4478 discloses that N-methylated cyclic amines (referred to here as imines) can be prepared in the gas phase over a copper catalyst. However, the space-time yields are generally less than 0.1 kg per 1 per h.

It is an object of the present invention to provide a better method of obtaining the substituted cyclic amines and to overcome the disadvantages of the known process.

We have found that this object is achieved by a novel and improved process for the preparation of N-substituted cyclic amines of the general formula I $$A \bigcirc N-R \qquad \text{I}$$

where A is an alkylene group or a $-(CH_2)_n-[-O-(CH_2)_m]_r$ group which may be monosubstituted or polysubstituted by radicals R without the radicals R in a defined compound having to be identical, R is alkyl, alkoxyalkyl, unsubstituted or alkyl-substituted or alkoxy-substituted cycloalkyl, cycloalkylalkyl, aryl or arylalkyl, n and m independently of one another are each from 2 to 8 and r is from 1 to 3, the $-(CH_2)_n-[O-(CH_2)_m 9_r$ group consisting of from 5 to 12 members, by reacting a primary amine of the general formula II $$R-NH_2 \qquad (II)$$

with a diol of the general formula III $$HO-A-OH \qquad (III)$$

where R and A have the abovementioned meanings, and hydrogen in the presence of a copper-containing hydrogenation/dehydrogenation catalyst at elevated temperatures and under super atmospheric pressure, wherein the reaction is carried out in the presence of a catalytic amount of a basic alkali metal or alkaline earth metal compound.

The N-substituted cyclic amines of the general formula I are obtainable by the following method:

The reaction is carried out by bringing a mixture of a primary amine II, a diol III and hydrogen into contact with a catalytic amount of a basic alkali metal or alkaline earth metal compound in the presence of a copper-containing hyrogenation/dehydrogenation catalyst, in accordance with the following equation:

$$R-NH_2 + HO-A-OH \longrightarrow A \bigcirc N-R + 2 H_2O$$

$$(II) \qquad (III) \qquad (I)$$

The reaction is carried out in the liquid phase, batchwise or, preferably, continuously, at from 150° to 300° C. and under from 40 to 300 bar.

The reaction mixture contains the primary amine II and the diol III in a molar ratio of from 0.2:1 to 5:1, preferably from 0.3:1 to 3:1, particularly preferably from 0.5:1 to 2:1.

Suitable basic alkali metal or alkaline earth metal compound are inorganic alkali metal or alkaline earth metal bases, preferably hydroxides and/or oxides of the alkali metals and/or alkaline earth metals, such as lithium hydroxide, sodium hydroxide, potassium hydroxide, magnesium hydroxide, calcium hydroxide, strontium hydroxide, barium hydroxide, lithium oxide, sodium oxide, potassium oxide, magnesium oxide, calcium oxide, strontium oxide, barium oxide or a mixture of these, particularly preferably sodium hydroxide and potassium hydroxide, as well as organic alkali metal or alkaline earth metal bases, such as alcoholates, for example the $C_1-C_4$-alcoholates, of the alkali metals and/or alkaline earth metals, such as sodium methylate, sodium ethylate, potassium methylate or potassium ethylate, particularly preferably sodium methylate.

They are used in catalytic amounts of from 0.01 to 10, preferably from 0.01 to 1, particularly preferably from 0.02 to 0.2, % by weight, based on the sum of primary amine II and diol III. They are advantageously dissolved or suspended in the alcohol used or are preferably dissolved in water.

Any water which may have been introduced as well as the resulting water of reaction should remain in the mixture during the reaction. The hydrogen partial pressure during the reaction is, as a rule, from 2 to 300, preferably from 50 to 250, particularly preferably from 100 to 250, bar.

If necessary, an inert gas, for example nitrogen or argon, preferably nitrogen, is additionally used.

The liquid phase reaction can be carried out, for example, as a suspension, trickle-bed or liquid phase reaction, at from 150° to 300° C. and under from 50 to 300 bar, preferably at from 180° to 260° C. and under from 100 to 250 bar. It is advisable for the sparingly volatile or solid primary amines II or diols III to be used in solution in an inert solvent, from 50 to 200, preferably from 100 to 150, ml of an inert solvent generally being sufficient per mole of II or III.

Suitable inert solvents are ethers, such as diethyl ether, methyl isopropyl ether, methyl tert-butyl ether, tetrahydrofuran and dioxane, aliphatic hydrocarbons, such n-pentane, the mixture of pentane isomers, n-hexane, the mixture of hexane isomers, petroleum ether and cyclohexane, aromatic hydrocarbons, such as benzene, toluene, the xylenes and their isomer mixtures, or mixtures of these solvents.

Particularly suitable hydrogenation/dehydrogenation catalysts are those whose catalytic activity is mainly attributable to copper and not less than 80% by weight of whose active material consists of this metal. Copper catalysts whose catalytically active material consists of more than 90% by weight of metallic copper are particularly preferred.

The copper can be used in the form of powder, chips or a skeleton catalyst (Raney copper), but it is advisable to prepare the catalyst by reduction of copper compounds, such as copper acetate, copper propionate or copper oxide, and the reduction may be carried out in situ using hydrogen, a metal hydride or an organic metal compound.

For example, catalysts disclosed in EP-A-No. 70 512, which are formed from copper formate under the reaction conditions, are suitable.

Other suitable catalysts are those obtained according to DE-A-No. 2 445 303, by adding an alkali metal carbonate to an aqueous solution containing a copper salt and an aluminum salt, for example in a molar ratio of Cu to Al of from about 0.2:1 to 1:1, and molding the resulting basic Cu/Al mixed carbonate into catalyst particles, such as spheres or extrudates, and then drying these at from 200° to 600° C. Under the reaction conditions, these particles form a porous skeleton of alumina and aluminum oxide hydoxide with an appropriately large surface layer of metallic copper.

It is also possible to use copper-containing supported catalysts, which are treated by impregnating a carrier, such as pumice, diatomaceous earth, silica gel or alumina, with a copper salt solution, drying the product and then reducing it, for example with hydrogen.

In addition to the main component, copper, the catalysts can also contain minor amounts of other components, for example cobalt and nickel.

In the batchwise procedure, the catalysts are preferably used in the form of finely divided suspensions. In the continuous process, it is advisable to use fixed-bed catalysts which are operated by the trickle-bed procedure or, preferably, by the liquid phase procedure in which the entire catalyst bed should be cohesively covered with liquid.

The amount of catalyst preferably corresponds to 10–150, in particular 20–70, g of copper per kg of reaction mixture in the batchwise suspension process, and preferably to 100–500, in particular 200–400, g of copper per kg of reaction mixture per hour for continuous operation over a fixed-bed catalyst.

In the batchwise procedure, the diol III with the catalyst suspended therein and a dissolved or suspended inorganic base in water can be initially taken and the amine II can be added gradually, at the rate at which the reaction proceeds at the reaction temperature under the chosen conditions. Particularly when the reactants are used in equimolar amounts, the components diol, amine, water and base can also b initially taken together.

In the continuous procedure, the diol III and the amine II in the chosen molar ratio are passed over a fixed-bed copper catalyst, and the inorganic base and the water may be dissolved or suspended in one or both of these components.

After the reaction, the resulting products are isolated from the reaction mixture by a conventional method, for example by distillation or extraction; unconverted starting materials are, if required, recycled to the reaction.

In the formulae I to III, the substituents have the following meanings:

A is alkylene, such as $C_4$–$C_{12}$-alkylene, e.g. —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$— and —$(CH_2)_{12}$— of which the alkylene groups of 4 to 8 carbon atoms are preferred, a —$(CH_2)_n$—[O—$(CH_2)_m$]$_r$ group, where n and m independently of one another are each from 2 to 8 and r is from 1 to 3, the —$(CH_2)_n$—[O—$(CH_2)_m$]$_r$ group consisting of from 5 to 12 members, and preferably n and m independently of one another each being from 2 to 4 and r being 1 or 2, such as —$(CH_2)_2$—O—$(CH_2)_2$—, —$(CH_2)_3$—O—$(CH_2)_2$—, —$(CH_2)_3$—O—$(CH_2)_3$—, —$(CH_2)_4$—O—$(CH_2)_2$—, —$(CH_2)_4$—O—$(CH_2)_3$—, —$(CH_2)_4$—O—$(CH_2)_4$— and —$(CH_2)_2$—O—$(CH_2)_2$—O—$(CH_2)_2$—.

A may be substituted by one or more of the radicals R blow, and the radicals R in a defined compound need not be identical. From 1 to 6 radicals R are preferred, from 1 to 4 being particularly preferred.

R is alkyl, such as straight-chain or branched $C_1$–$C_{30}$-alkyl, preferably straight-chain or branched $C_1$–$C_{20}$-alkyl, particularly preferably straight-chain or branched $C_1$–$C_{12}$-alkyl, such as methyl, ethyl, n-propyl, isopropyl, n-butyl, isobutyl, sec-butyl, tert-butyl, n-pentyl, isopentyl, sec-pentyl, tert-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, alkoxyalkyl, preferably $C_2$–$C_{20}$-alkoxyalkyl, such as methoxymethyl, ethoxypropyl and butoxydecyl, cycloalkyl, preferably $C_3$–$C_{20}$-cycloalkyl, particularly preferably $C_3$–$C_8$-cycloalkyl, such as cyclopropyl, cyclobutyl, cyclopentyl, cyclohexyl, cycloheptyl and cyclooctyl, alkylcycloalkyl, preferably $C_4$–$C_{20}$-alkylcycloalkyl, such as methylcyclopropyl, isopropylcyclohexyl and dodecylcyclohexyl, cycloalkylalkyl, preferably $C_4$–$C_{20}$-cycloalkylalkyl, such as cyclopropylmethyl, cyclopentylmethyl, cyclohexylmethyl, cyclopropylethyl, cyclopentylethyl and cyclohexylethyl, aryl, such as phenyl, 1-naphthyl, 2-naphthyl, 1-anthyl, 2-anthyl and 9-anthyl, preferably phenyl, and arylalkyl, preferably $C_7$–$C_{20}$-arylalkyl, particularly preferably $C_7$–$C_{10}$-phenylalkyl, such as benzyl, phenethyl or phenyldecyl.

Examples of end products of the formula I are: N-methylpyrrolidine, N-ethylpyrrolidine, N-methylpiperidine, N-ethylpiperidine, N-methylmrrpholine, 1-methyl-1-azacycloundecane and N-n-butylmorpholine.

Examples of starting materials of the formula II are: methylamine, ethylamine, n-propylamine, isopropylamine, n-butylamine, isobutylamine, n-dodecylamine, aniline and p-toluidine.

Examples of starting materials of the formula III are:
butane-1,4-diol,
3-methylpentane-1,5-diol,
diethylene glycol (3-oxapentane-1,5-diol),
dibutylene glycol (5-oxanonane-1,9-diol),
triethylene glycol (3,5-dioxaheptane-1,7diol),
1,3-ipropylene glycol (4-oxaheptane-1,7-diol),
dipropylene glycol (1,5-dimethyl-3-oxapentane-1,5-diol), 5-oxanonane-1,9-diol and
hexane-2,5-diol.

In general, suitable diols III are those having primary or secondary hydroxyl groups, in particular those having primary hydroxyl groups.

The secondary amines of the general formula I which can be prepared by the novel process are, for example, reactants or specific acid acceptors in the synthesis of drugs, of active ingredients for crop protection and of dyes, or are basic catalysts, for example for the preparation of polyurethanes.

The Examples which follow illustrate the novel process without restricting the invention.

EXAMPLES

Preparation of the Catalyst

A mixed carbonate according to Example 1 of DE-A-24 45 303 was precipitated from an aqueous solution of copper nitrate and aluminum nitrate with sodium bicarbonate (molar ratio of copper to aluminum 1:1.2), molded into cylinders having a length of 3 mm and a diameter of 3 mm, dried and then introduced into the reactor and treated therein at from 180° to 200° C. with 300 ml/hour of a 0.01% strength by weight methanolic sodium methylate solution under a hydrogen pressure of 50 bar.

EXAMPLE 1

Preparation of N-methylpiperidine 280 ml/hour of a mixture which consisted of 1,040 g of pentane-1,5-diol and 310 g of methylamine and 10 g of 45% strength aqueous potassium hydroxide solution were passed, at 245° C., under a total pressure of 250 bar and under a hydrogen partial pressure of 120 bar, through a tube reactor which had a diameter of 3.2 cm and a height of 125 cm and contained a bed of 700 ml of the catalyst prepared above. N-methylpiperidine was obtained in 95% yield.

EXAMPLE 2

Preparation of N-(n-butyl)-pyrrolidine 11.7 kg of butane-1,4-diol were reacted with 7.3 kg of n-butylamine similarly to Example 1. N-(n-butyl)-pyrrolidine was obtained in 96% yield.

EXAMPLE 3

Preparation of N-methylmorpholine 1,060 g of diethylene glycol were reacted with 310 g of methylamine similarly to Example 1. N-methyl passed, morpholine was obtained in 98% yield.

We claim:
1. A process for the preparation of an N-substituted cyclic amine of the formula I

where A is an alkylene group or a $-(CH_2)_n-[-O-(CH_2)_m]_r$ group which may be monosubstituted or polysubstituted by radicals R without the radicals R in a defined compound having to be identical, R is lkyl, alkoxyalkyl, unsubstituted or alkyl-substituted or alkoxy-substituted cycloalkyl, cycloalkylalkyl, aryl or arylalkyl, n nd m independently of one another are each from 2 to 8 and r is from 1 to 3, the $-(CH_2)_n-[O-(CH_2)_m]_r$ group consisting of from 5 to 12 members, by reacting a primary amine of the formula II $$R-NH_2 \qquad (II)$$

with a diol of the formula III $$HO-A-OH \qquad (III)$$

where R and A have the abovementioned meanings, and hydrogen in the presence of a copper-containing hydrogenation/dehydrogenation catalyst at elevated temperatures and under super atmospheric pressure, wherein the reaction is carried out in the presence of a catalytic amount of a basic alkali metal or alkaline earth metal compound.

2. A process as claimed in claim 1, wherein from 0.01 to 10% by weight, based on the sum of a primary amine II and diol III, of one or more hydroxides and/or oxides and/or $C_1-C_4$-alcoholates of the alkali metals and/or of the alkaline earth metals are used as basic compounds.

3. A process as claimed in claim 1, wherein the reaction is carried out using a molar ratio of primary amine II to diol III of from 0.2:1 to 5:1.

4. A process as claimed in claim 1, wherein the reaction is carried out using a molar ratio of primary amine II to diol III of from 0.5:1 to 2:1.

5. A process as claimed in claim 1, wherein the hydrogenation/dehydrogenation catalyst used is one which essentially contains copper as the catalytically active metal component.

6. A process as claimed in claim 1, wherein the reaction is carried out without removal of the water of reaction.

7. A process as claimed in claim 1, wherein the reaction is carried out under from 50 to 300 bar.

* * * * *

UNITED STATES PATENT AND TRADEMARK OFFICE
CERTIFICATE OF CORRECTION

PATENT NO. : 4,910,304

DATED : March 20, 1990

INVENTOR(S) : Roman Fischer, Herbert Mueller, Dieter Voges

It is certified that error appears in the above-identified patent and that said Letters Patent is hereby corrected as shown below:

In Claim 1, at line 14, change "lkyl" to --alkyl--.

Signed and Sealed this

Twenty-sixth Day of March, 1991

*Attest:*

HARRY F. MANBECK, JR.

*Attesting Officer*      *Commissioner of Patents and Trademarks*